United States Patent
Erickson et al.

(10) Patent No.: US 10,159,569 B2
(45) Date of Patent: Dec. 25, 2018

(54) MINIMALLY INVASIVE ATRIO-VENTRICULAR VALVE TREATMENT BY CHORDAE ADJUSTMENT

(71) Applicant: Lars Erickson, Newton, MA (US)

(72) Inventors: Lars Erickson, Newton, MA (US); Wayne Boucher, Manchester, NH (US)

(73) Assignee: Lars Erickson, Newton, MA (US)

( * ) Notice: Subject to any disclaimer, the term of this patent is extended or adjusted under 35 U.S.C. 154(b) by 253 days.

(21) Appl. No.: 15/097,181

(22) Filed: Apr. 12, 2016

(65) Prior Publication Data
US 2017/0290663 A1    Oct. 12, 2017

(51) Int. Cl.
A61F 2/24    (2006.01)

(52) U.S. Cl.
CPC .......... A61F 2/2457 (2013.01); A61F 2/2466 (2013.01)

(58) Field of Classification Search
CPC ...... A61F 2/24; A61F 2/02; A61F 2/08; A61F 2/0805; A61B 17/00; A61B 17/04; A61B 17/08; A61B 17/122; A61B 17/32056; A61B 17/12; A61B 17/12004; A61B 17/12009; A61B 2017/00358; A61B 17/00234; A61B 2017/00225
See application file for complete search history.

(56) References Cited

U.S. PATENT DOCUMENTS

| | | | |
|---|---|---|---|
| 5,897,565 A | 4/1999 | Foster | |
| 5,964,758 A * | 10/1999 | Dresden | A61B 18/1445 606/45 |
| 6,352,503 B1 | 3/2002 | Matsui | |
| 6,629,534 B1 | 7/2003 | Goldfarb | |
| 6,610,072 B1 | 8/2003 | Christy | |
| 6,626,899 B2 | 9/2003 | Houser | |
| 6,740,107 B2 | 5/2004 | Loeb | |
| 6,752,813 B2 | 6/2004 | Goldfarb | |
| 7,608,091 B2 | 10/2009 | Goldfarb | |
| 7,635,386 B1 | 12/2009 | Gammie | |
| 7,666,204 B2 | 2/2010 | Thornton | |
| 7,704,269 B2 | 4/2010 | St. Goar | |
| 7,758,596 B2 | 7/2010 | Mehmet | |
| 7,998,151 B2 | 8/2011 | St. Goar | |
| 8,252,050 B2 | 4/2012 | Maisano | |
| 8,292,884 B2 | 10/2012 | Levine | |
| 8,500,800 B2 | 8/2013 | Maisano | |
| 8,734,505 B2 | 5/2014 | Goldfarb | |

(Continued)

*Primary Examiner* — Jonathan Miles
*Assistant Examiner* — George J Ulsh
(74) *Attorney, Agent, or Firm* — Bookstein IP Law

(57) ABSTRACT

Minimally invasive catheters and methods are provided for adjusting the chordae associated with an atrio-ventricular valve. The catheter is adapted to engage a selected chord and draw it into a pair of transversely spaced, receptive clamps at the distal end of the catheter in readiness to be clamped The clamps are part of a prosthetic cord assembly that includes the clamps and a cord attached to each of the clamps. The effective length of a natural chord can be increased by employing a long prosthetic cord and clamping and severing the natural chord between the clamps. The effective length of a chord can be decreased by drawing the natural chord into the distal end of the catheter to a hairpin shape and clamping the legs of the hairpin-restrained chord. The chord need not be severed when its effective length is being reduced.

9 Claims, 16 Drawing Sheets

(56) References Cited

U.S. PATENT DOCUMENTS

| | | |
|---|---|---|
| 8,778,016 B2 | 7/2014 | Janovsky |
| 8,790,394 B2 | 7/2014 | Miller |
| 8,852,213 B2 | 7/2014 | Gammie |
| 8,808,658 B2 | 8/2014 | Maisano |
| 8,888,844 B2 | 11/2014 | Eliasen |
| 8,894,705 B2 | 11/2014 | Eliasen |
| 8,956,406 B2 | 2/2015 | Subramanian |
| 8,961,597 B2 | 2/2015 | Subramanian |
| 8,992,606 B2 | 3/2015 | Baliarda |
| 9,011,515 B2 | 4/2015 | Schweich, Jr. |
| 9,044,246 B2 | 6/2015 | Goldfarb |
| 9,050,188 B2 | 6/2015 | Schweich, Jr. |
| 9,060,858 B2 | 6/2015 | Thornton |
| 9,125,739 B2 | 9/2015 | Paniagua |
| 9,125,742 B2 | 9/2015 | Yoganathan |
| 9,155,622 B2 | 10/2015 | Baliarda |
| 9,161,837 B2 | 10/2015 | Kapadia |
| 9,005,279 B2 | 12/2015 | Gabbay |
| 9,198,757 B2 | 12/2015 | Schroeder |
| 9,232,995 B2 | 1/2016 | Kovalsky |
| 9,232,998 B2 | 1/2016 | Wilson |
| 9,232,999 B2 | 1/2016 | Maurer |
| 9,241,790 B2 | 1/2016 | Lane |
| 9,248,014 B2 | 2/2016 | Lane |
| 2001/0049509 A1 | 12/2001 | Sekine |
| 2007/0118151 A1 | 5/2007 | Davidson |
| 2007/0270643 A1* | 11/2007 | Lu ............... A61B 17/0206 600/114 |
| 2009/0143639 A1* | 6/2009 | Stark ............... A61B 1/018 600/102 |
| 2010/0023118 A1 | 1/2010 | Medlock |
| 2014/0114404 A1* | 4/2014 | Gammie ........... A61B 17/0401 623/2.11 |
| 2015/0150634 A1* | 6/2015 | Isoda ............... A61B 17/29 606/130 |
| 2016/0015410 A1* | 1/2016 | Asirvatham ........ A61B 17/29 606/49 |

\* cited by examiner

MINIMALLY INVASIVE ATRIO-VENTRICULAR VALVE TREATMENT BY CHORDAE ADJUSTMENT

FIELD OF INVENTION

The invention relates generally to minimally invasive devices and techniques for adjusting the closing positions of the leaflets of a malfunctioning atrio-ventricular (A-V) valve by selectively adjusting the length of one or more chordae associated with the valve.

BACKGROUND

The heart has a left side and a right side, each side including an atrium and a ventricle. The atria receive blood returning through veins to the heart and the ventricles pump blood away from the heart, through arteries, to circulate blood through the body. The blood returns to the right side of the heart through the venous system. The heart also includes four one-way valves (aortic, pulmonary, mitral and tricuspid) that function to maintain unidirectional blood flow as the heart contracts in a pumping stroke (systole) and then relaxes and expands to fill the ventricles (diastole). Each side has an A-V valve (the tricuspid and mitral valves) that controls flow from its atrium to its associated ventricle, and each ventricle has an output valve (the pulmonary valve and aortic valve). When the heart muscle contracts (systole) blood is pumped from both ventricles through their respective output valves. Oxygenated blood from the left ventricle is pumped through the aortic valve to the aorta and branching arteries while blood from the right ventricle is pumped through the pulmonary valve to the lungs where it is oxygenated. The oxygenated blood from the lungs is returned to the heart and is received in the left atrium. The right atrium receives return blood via the venous system. During diastole, blood in each atrium is drawn through its associated A-V valve to refill its associated ventricle in readiness for the next cardiac contraction.

In a healthy, properly functioning heart the A-V valves close fully during systole to prevent backflow of blood from the ventricles to the atria as the ventricles contract. Each of the mitral and tricuspid valves is defined by an arrangement of leaflets flexibly attached to an annular supportive ring. The leaflets have free marginal edges that engage each other during systole to close the flow path between the atrium and its associated ventricle. The closed positions of the leaflets of the A-V valves are limited and defined by tendonous chordae that are attached, at one end, to papillary muscles in the lower portions of the ventricles and, at their upper ends, to the undersides of the leaflets of the A-V valves as suggested in FIG. 2. In a healthy heart, the lengths of the chordae limit the movement of the leaflets during systole so that as the blood pressure in the ventricle increases, the free, marginal edges of the leaflets engage each other to close the valve and prevent backflow from the ventricles to the atria. During diastole the leaflets are not restrained by the chordae and their marginal edges are free to separate to allow blood flow from the atria to the associated ventricle.

Various cardiac-related diseases, however, may affect the heart by distorting its shape such that the leaflets of the mitral (left side) or tricuspid (right side) valve may not close properly and may result in backflow during systole. Deformation in the shape or structure of the heart wall may effect a change in the relative position of the papillary muscles to which the chordae are attached. That, in turn, affects the positions of the valve leaflets so that they may not close fully during systole. For example, such heart muscle deformation may occur in patients with coronary artery disease or those who have had myocardial infarction (heart attack) and are prone to developing mitral valve regurgitation due to chordal tethering, which results in reduced cardiac efficiency. That, in turn, may lead to further cardiac complications such as enlargement of the atria and/or ventricles, pulmonary hypertension, heart failure and other problems. Various procedures and techniques have been employed and proposed to improve the functioning of a compromised A-V valve. These include, for example, complex, invasive, open-heart surgery to surgically repair the valve, as by reforming or reinforcing the shape of the annulus of the valve or by selectively attaching portions of the marginal edges of leaflets together. Other remedies may involve replacement of an A-V valve with a mechanical valve or a bioprosthetic valve. Less invasive, catheter-based procedures also have been proposed, including adjustment of the chordae of the mitral or tricuspid valve. It is among the objects of the invention to provide catheter-based devices to facilitate minimally invasive adjustment of the length of chordae of A-V valves in order to adjust the closed position of the leaflets of the valve and restore the function to a malfunctioning A-V valve.

SUMMARY

In order to adjust the effective length of the chordae of a malfunctioning A-V valve, catheters are provided to engage and increase or decrease the effective length of one or more selected chordae so that the associated leaflet or leaflets will close properly. The catheterization procedure should be done in conjunction with imaging technology, for example, ultrasound, trans-esophageal echocardiography, intracardiac echocardiography, fluoroscopy, angioscopy, catheter based magnetic resonance imaging, computed tomography and the like. The imaging technique may enable visualization of blood flow and particularly how the adjustment of the chordae affects backflow through the valves. If backflow has not been adequately corrected the catheter can be reconfigured and manipulated to make further adjustments until the desired result is achieved.

In one aspect of the invention an elongate catheter is configured to lengthen a chord by severing the chord and reconnecting the severed ends with a longer prosthetic cord assembly to increase the effective length of that chord. The catheter is adapted to be advanced through a patient's vasculature to place the distal end of the catheter within the ventricle associated with the A-V valve to be treated. A prosthetic cord assembly including a pair of releasable clamps is carried at the distal end of the catheter. The clamps are spaced laterally at diametrically opposite positions on the catheter and are open in a distal direction in order to receive a chord oriented transversely to the axis of the catheter. The clamps are connected to each other by a prosthetic cord, the length of which is selected to correspond to the degree of adjustment to be made to the natural chord. The catheter also includes a snare that can be extended axially between the clamps and beyond the distal end of the catheter to engage a selected natural chord. The snare and engaged chord then can be retracted to draw that chord into the open clamps. The clamps then are caused to close to clamp the natural chord and a severing element carried by the catheter then is operated to sever the natural chord between the clamps. The clamps then are released from the catheter. Upon release, the effective length of the selected chord is increased in an amount determined by the length of the prosthetic cord assembly. The catheter then may be withdrawn. Should it be desirable to lengthen (or shorten) additional of the chordae another catheter may be introduced or the original catheter may be reloaded with another cord assembly. As used in this specification and claims, the term "chord" refers to one or more of a patients's natural chordae tendineae and the term "cord" refers to a prosthetic cord that connects clamps to each other.

The clamps may be spring biased to close automatically upon removal of a restraining element or, in an alternative arrangement, the clamps may be deformable from an open to a closed, securely clamped configuration. In either case, the clamps must maintain a secure hold on the chord.

In another aspect of the invention, the catheter may be configured to shorten the effective length of a selected chord. To that end a catheter includes an extendable and retractable snare and a chord clamping arrangement. The snare is employed to engage a selected chord and to draw the chord into the catheter, causing the chord to be doubled in a hairpin shape and effectively shortening the effective length of the chord. The clamping arrangement then is operated to clamp the doubled portion of the chord to secure the chord in its effectively shortened length.

In another aspect of the invention catheter-based methods are provided to increase or decrease the effective length of one or more chordae to restore the ability of an associated A-V valve to close and reduce or prevent back flow. As used herein, the term "effective length" is intended to mean the length of a natural chord as modified by use of the invention. Ideally "effective length" would be an adjusted length that would enable the associated A-V valve leaflets to coapt during systole without backflow.

The various objects and advantages of the invention will be appreciated more fully from the following detailed description with reference to the accompanying drawings.

IN THE DRAWINGS

FIGS. 14-18 illustrate the sequential steps of operation of the second embodiment of the invention and in which

DETAILED DESCRIPTION

Figure 1:
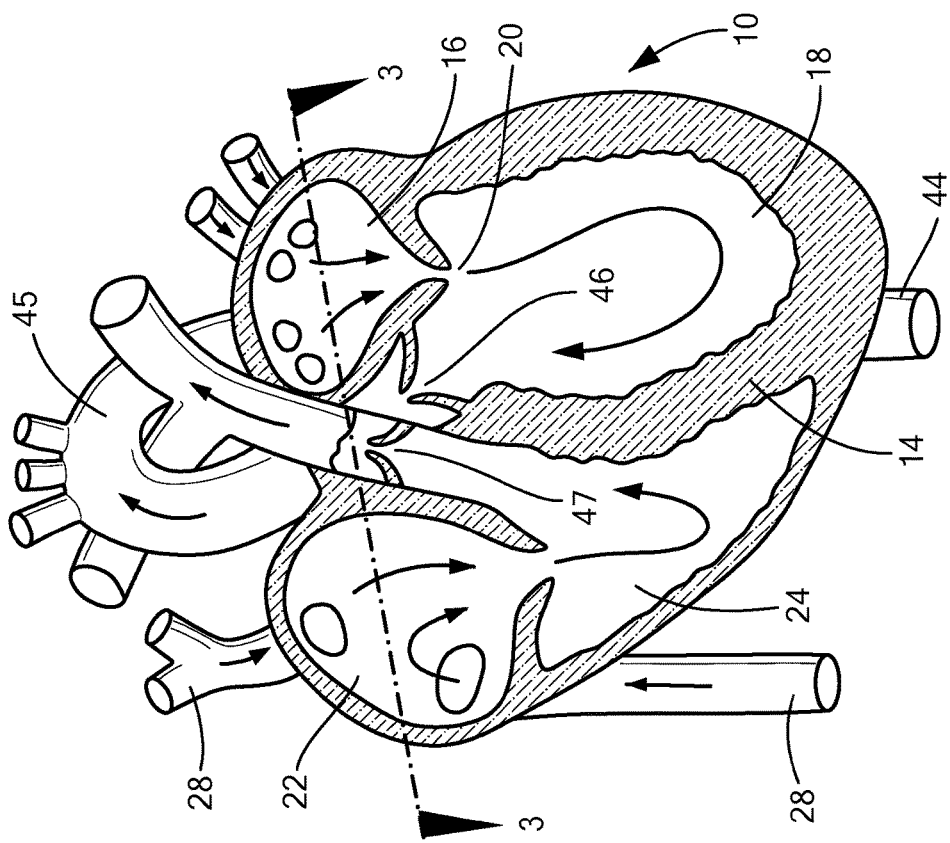
FIG. 1 is a diagrammatic sectional illustration of a heart showing the right and left sides and the four valves that control the direction of blood flow.

FIG. 1 shows the anatomy of the heart and the direction of blood flow. The heart has a left side 10 and a right side 12, the sides being separated by a septum 14. The left side, which provides the primary pumping function, includes a left atrium 16 that receives oxygenated blood returning to the heart from the lungs and a left ventricle 18 that receives oxygenated blood from the left atrium 16. The left atrium 16 and left ventricle 18 are separated by the mitral valve 20 that, when functioning normally, permits flow in one direction, from the atrium 16 to the ventricle 18, as indicated by the arrows.

The right side 12 of the heart, which receives return blood and directs it to the lungs, includes the right atrium 22, the right ventricle 24 and a tricuspid valve 26 between the right atrium and right ventricle. The right atrium receives blood returning to the heart through the venous system 28 and blood flows from the right atrium 22 to the right ventricle 24 through the tricuspid valve 26. When functioning normally, the tricuspid valve 26 permits flow in only one direction, from the right atrium 22 to the right ventricle 24.

Figure 2:
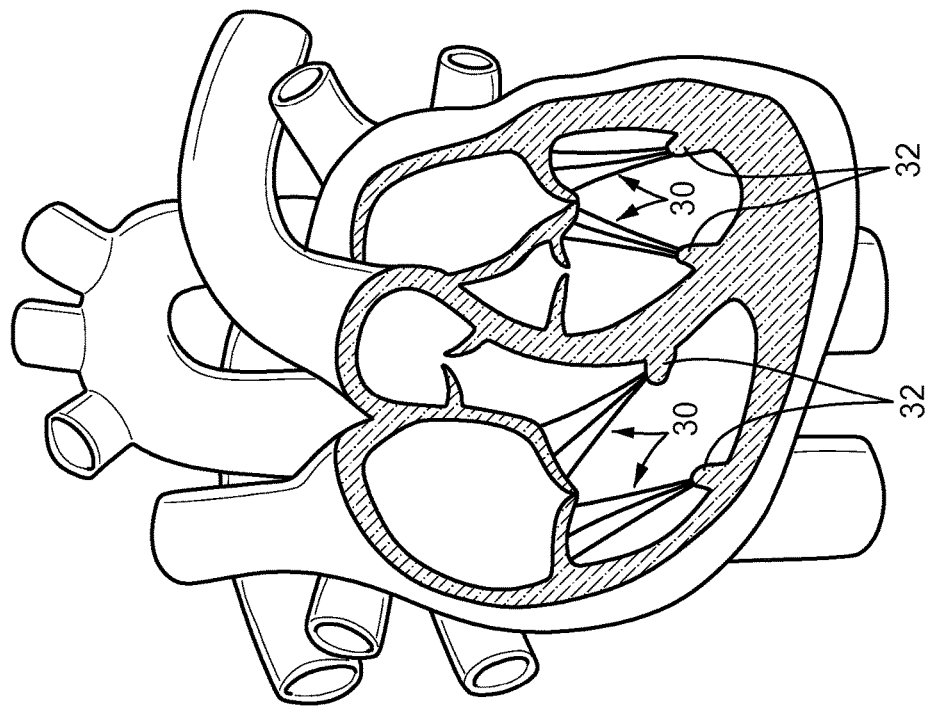
FIG. 2 is a diagrammatic, cut-away of a heart illustrating the arrangement of chordae and their associated atrio-ventricular valves.
Figure 3:
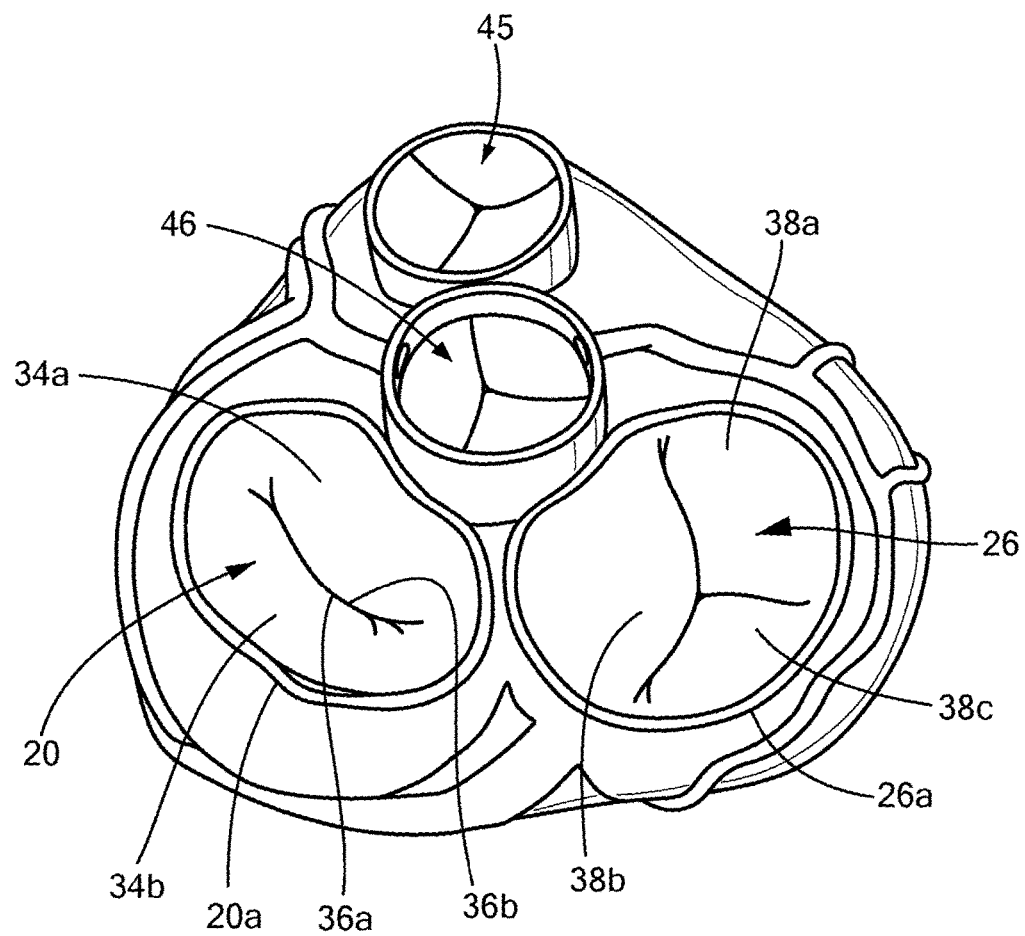
FIG. 3 is a diagrammatic plan sectional view of the heart as seen along the line 3-3 of FIG. 1 and showing the arrangement of the four cardiac valves with all of the valve leaflets closed to show how their marginal edges coapt when closed.

The structure of each of the A-V valves includes leaflets that open freely in response to pressure differential developed during diastole, as the heart expands from its contracted state. The leaflets of the mitral valve 20 are attached flexibly to an annular ring 20a and the leaflets of the tricuspid valve are attached to another annular ring 26a. During systole, however, the extent of leaflet movement is restrained by a number of tendon-like chordae arranged in a parachute-like array (shown diagrammatically at 30 in FIG. 2) in each ventricle that extend from a papillary muscle 32 or the interior of the ventricle wall to the underside or margin of the leaflets that define the associated A-V valve. In a healthy heart, the chordae 30 limit the movement of the leaflets so that the marginal free edges of the leaflets coapt as shown in FIGS. 2 and 3. However, in the case of a heart with impaired function the shape of the heart may become altered such that one or more of the chordae no longer allow the leaflets to close properly, resulting in backflow of blood from the ventricle to the atrium during systole. Backflow results in reduced pumping efficiency.

The mitral valve 20 has two semilunar leaflets including an anterior leaflet 34a and a posterior leaflet 34b as seen in FIG. 3. In a healthy heart the marginal edges 36a, 36b of the leaflets 34a, 34b coapt to close the valve during systole and open during diastole. In an impaired heart the leaflets may not close properly resulting in valve regurgitation or prolapse. The tricuspid valve 26 of the right side of the heart has three leaflets 38a, 38b, and 38c with associated chordae 30, functions similarly to the mitral valve, and is subject to similar malfunction.

Figure 4:
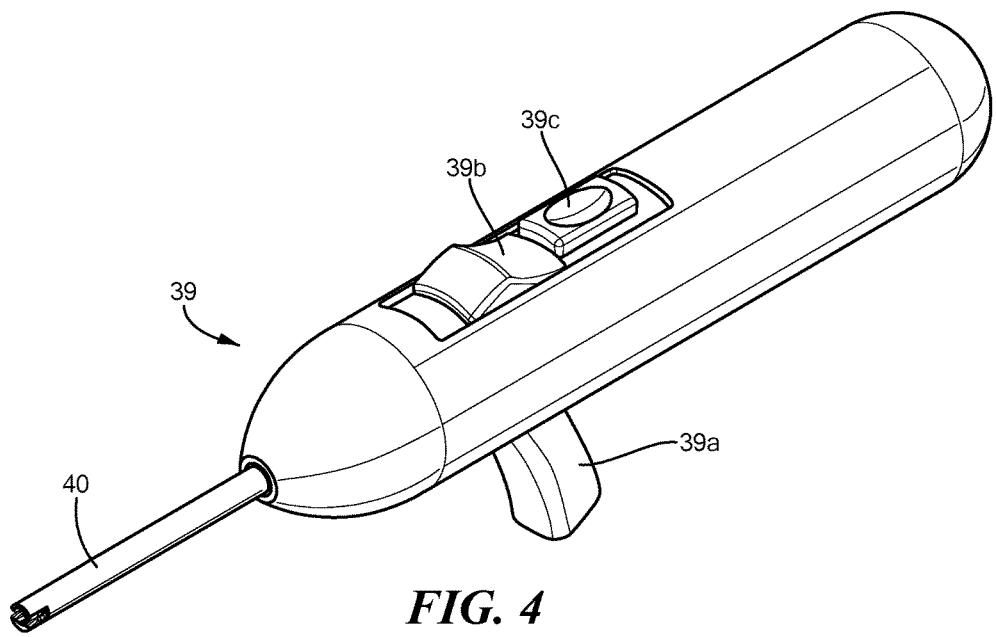
FIG. 4 is an illustration of a control handle at the proximal end of an embodiment of the invention.

A malfunctioning A-V valve may be corrected by a procedure to shorten or lengthen the effective length of selected of the chordae associated with that valve so that the marginal edges of the valve leaflets coapt during systole. FIGS. 5-12 show the distal region of one embodiment of a catheter adapted to increase the effective length of one or more chords 30 sufficiently so that the margins of the leaflets coapt properly during systole. Adjustments to the valve leaflets may require adjustment to the length of several chordae, depending on the condition and anatomy of a particular patient. The catheter preferably includes an elongate, flexible outer shaft 40 and an inner coaxial shaft 41 slidably disposed in a central lumen 43 of the outer shaft 40. The catheter has proximal and distal ends and may include a handle 39 with controls 39a, 39b and 39c at the proximal end to control operation of the instrumentalities at the distal end (FIG. 4). The catheter components may be constructed from a variety of materials commonly used in catheters and should be dimensioned in association with the selection of materials to be advanced through the patient's cardiovascular system. The catheter may be advanced by any of numerous, well-known approaches to place the distal end 42 of a catheter within a ventricle 18, 24 to be treated, as will be appreciated by those skilled in the art. For example, to reach the left side 10 of the heart to treat a malfunctioning mitral valve 20, the catheter may be advanced through a guide catheter (not shown) retrograde from a percutaneous puncture in the femoral artery, through the aorta 44 and aortic valve 46 and into the left ventricle 18. This can be performed while the heart is beating and avoids the complexities of placing the patient on extracorporeal support such as a heart-lung machine, as would be the case in open-heart surgery. Typically, a guiding catheter (not shown) and associated guide wires (not shown) may be employed using well known techniques (e.g., Seldinger) to guide the catheter through the aorta 44, aortic arch 45 and aortic valve 46 into the left ventricle 18. The inner shaft 41 may be provided with one or more lumens 50 to receive guide wires, facilitate flushing, injection of contrast agent and the like. The catheter and/or a guide catheter may be configured to be steerable to facilitate positioning the catheter with respect to the chordae. Other approaches to reach the left ventricle 18 also may be employed including access from the right side 12 of the heart and through the atrial septum 14 and then left atrium 16 and then through the mitral valve 20 into the left ventricle 18, or access through the apex 48 of the heart. Although it should be understood that the following description of the invention is in the context of repairing a mitral valve 20, the same principles and description applies with respect to a catheter for treatment of the tricuspid valve 26.

The procedure is performed under visualization as described above so that the clinician can determine the positions of the distal end 42 of the catheter as well as the valve leaflets 36a, 36b and associated chordae 30 as well as to visualize blood flow through the valve and, particularly, whether and to what degree backflow is present during systole.

Figure 6:
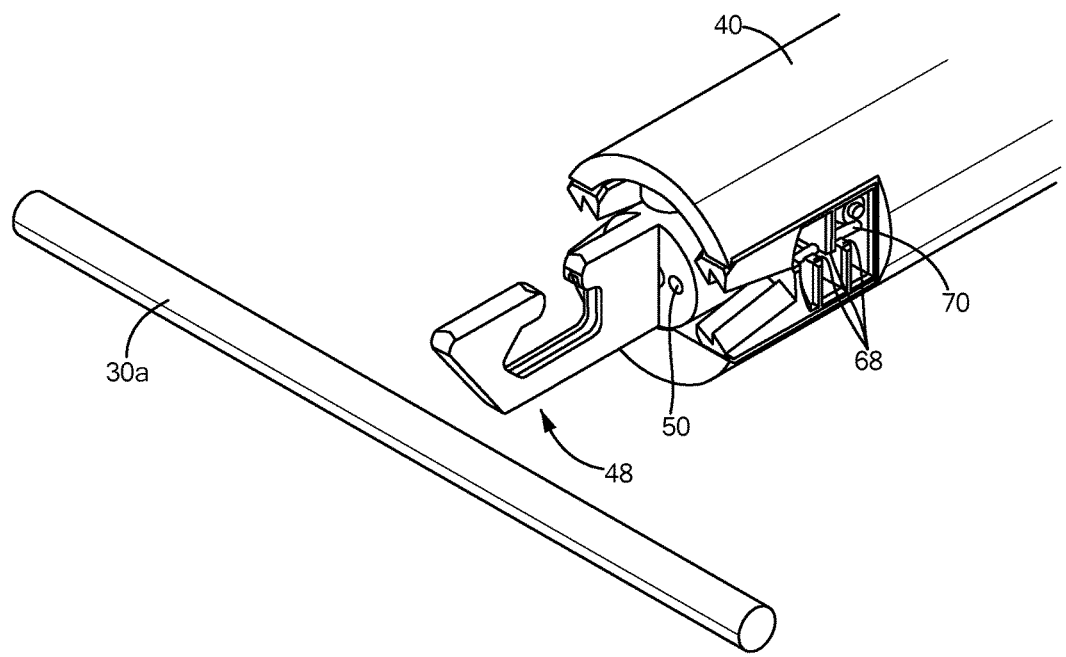
FIG. 6 is an illustration of the distal end of the catheter of one embodiment of the invention in which the snare is extended to engaged a selected chord.
Figure 7:
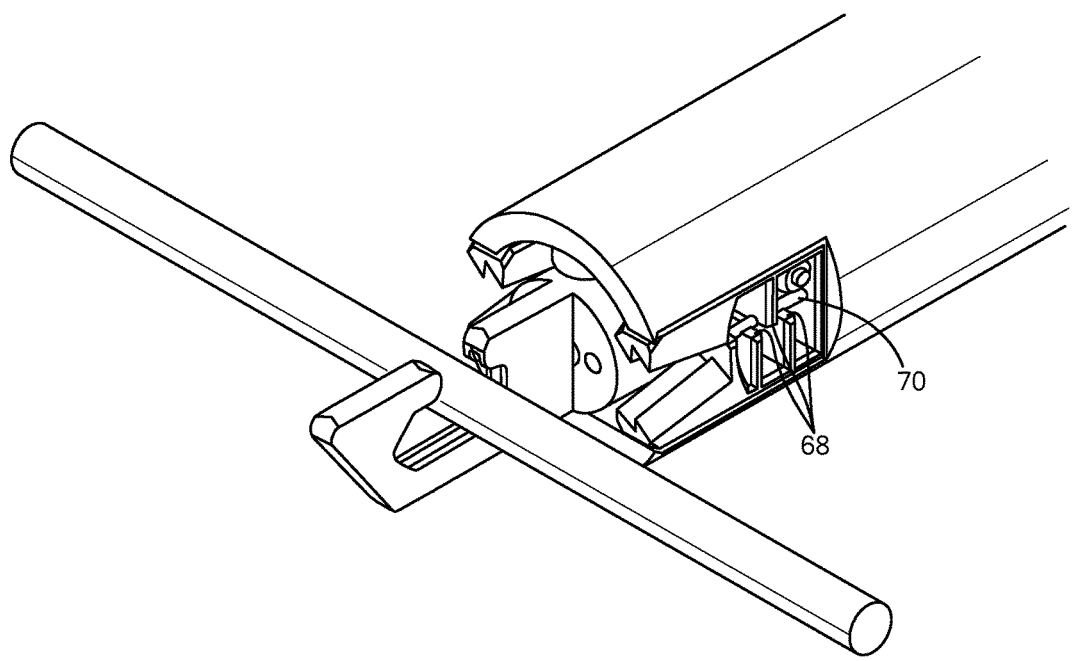
FIG. 7 is an illustration of the distal end of the catheter of one embodiment of the invention showing the chord engaged by the snare.
Figure 8:
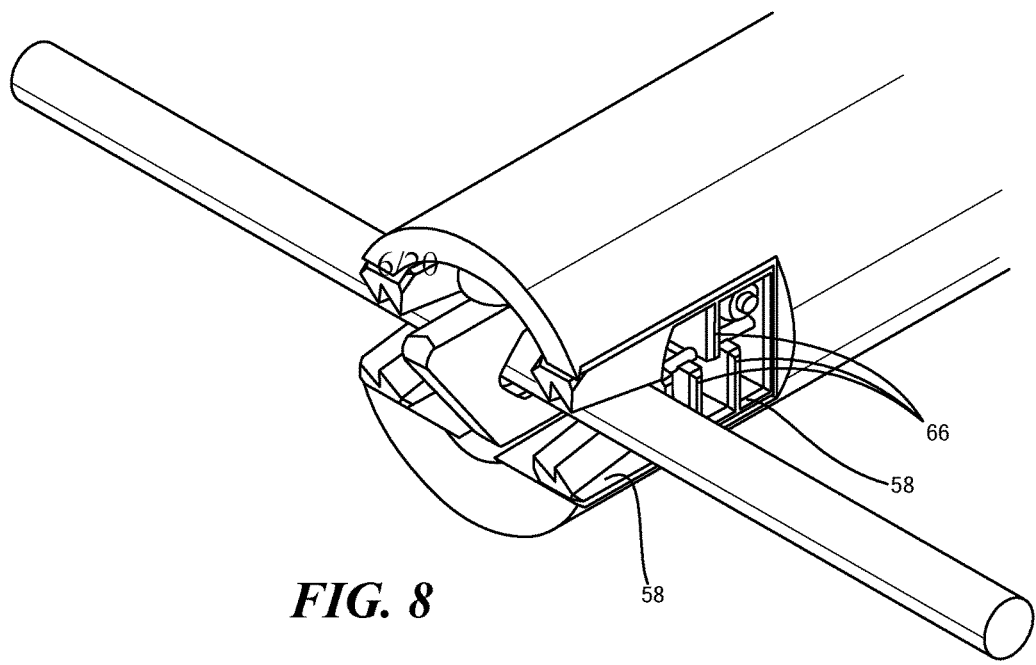
FIG. 8 is an illustration of the distal end of the catheter of one embodiment of the invention showing the snare and captured chord retracted into the catheter with the chord oriented transversely of the catheter axis and disposed within the clamps.

In order to engage a selected chord the catheter includes a snare 48 mounted to the distal end of the inner shaft 41. The snare 48 can be extended distally beyond the distal end of the catheter as shown in FIG. 6 by operating the control handle to move the inner shaft distally. The snare 48 may be configured in somewhat of a hook shape to receive and engage a selected chord to be adjusted. With a chord engaged by the snare (FIG. 7), the control handle is operated to retract the inner shaft 41 and snare 48 proximally into the distal end of the catheter (FIG. 8).

Figure 5:
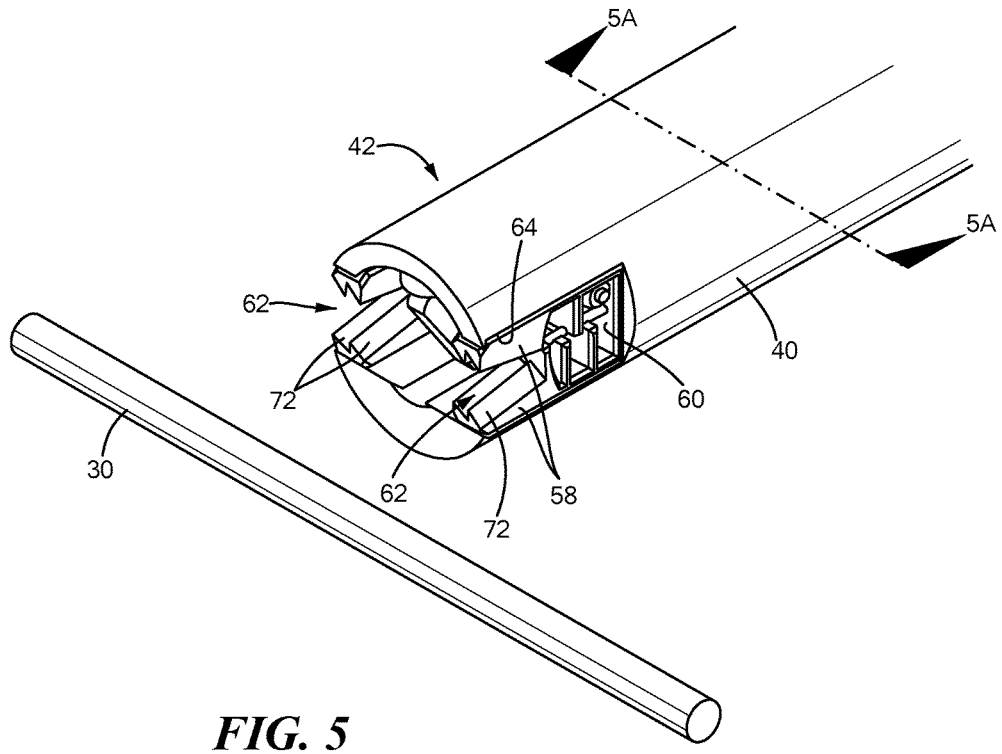
FIG. 5 is an illustration of the distal end of the catheter of one embodiment of the invention.
Figure 5A:
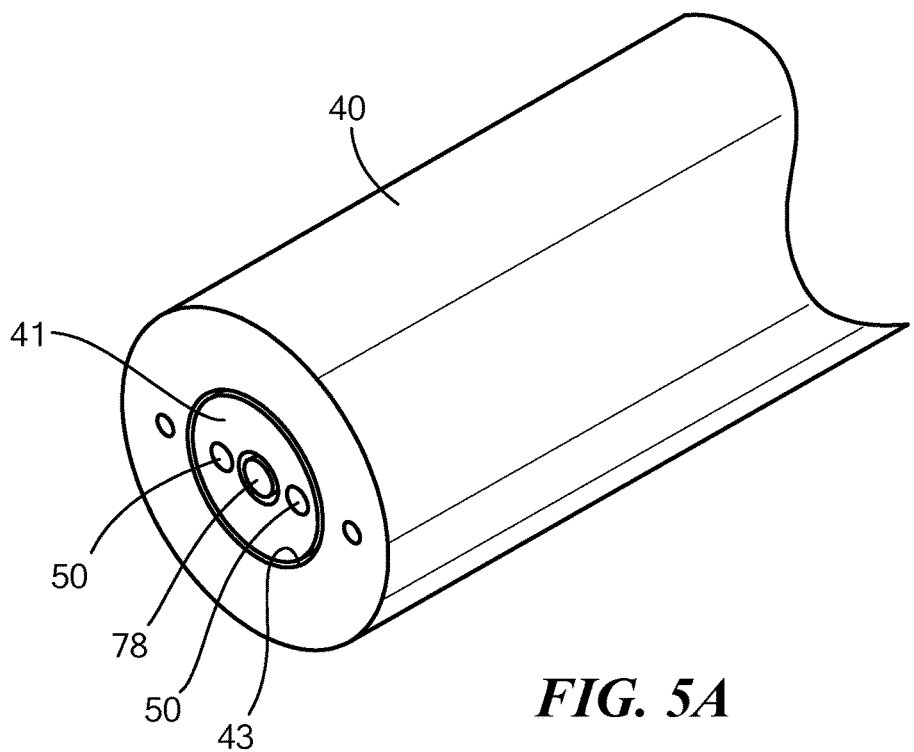
FIG. 5A is an illustration of the catheter of FIG. 5 truncated along the line 5A-5A of FIG. 5 to illustrate the cross-section of the catheter.
Figure 5B:
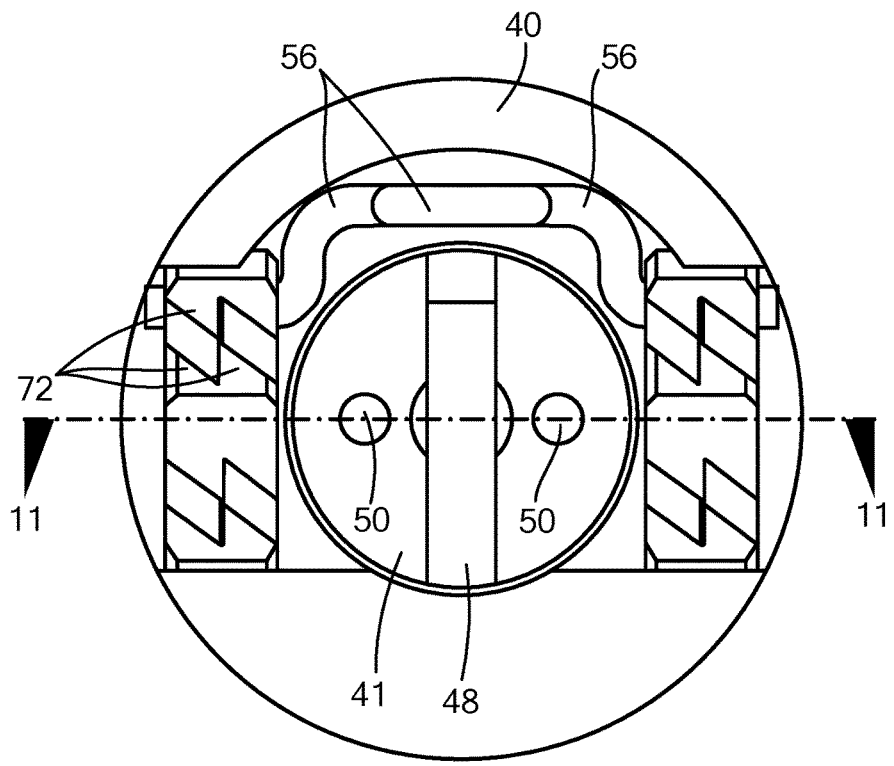
FIG. 5B is an end view of the catheter of FIG. 5.
Figure 16:
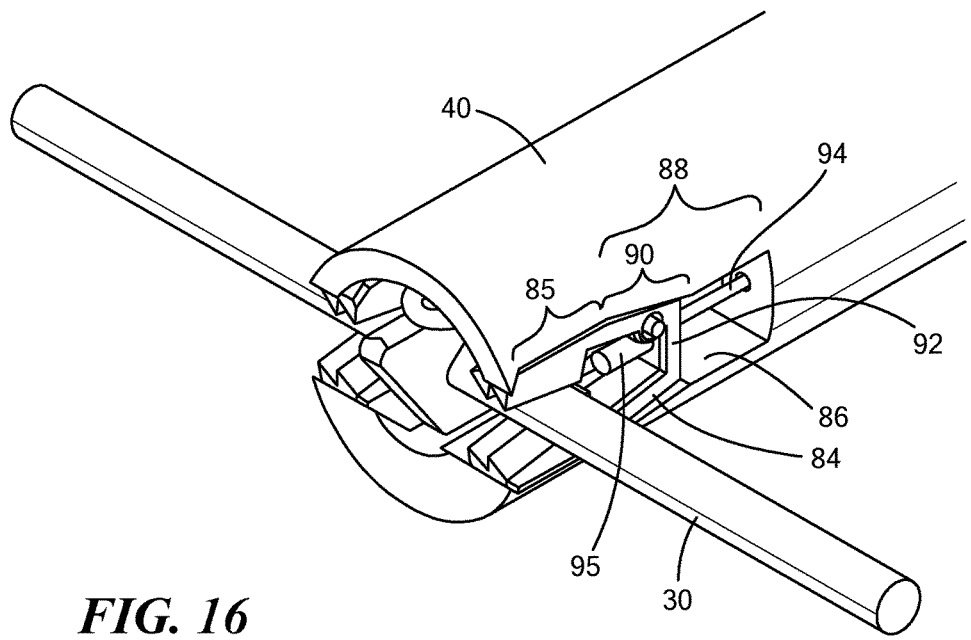
Figure 16A:
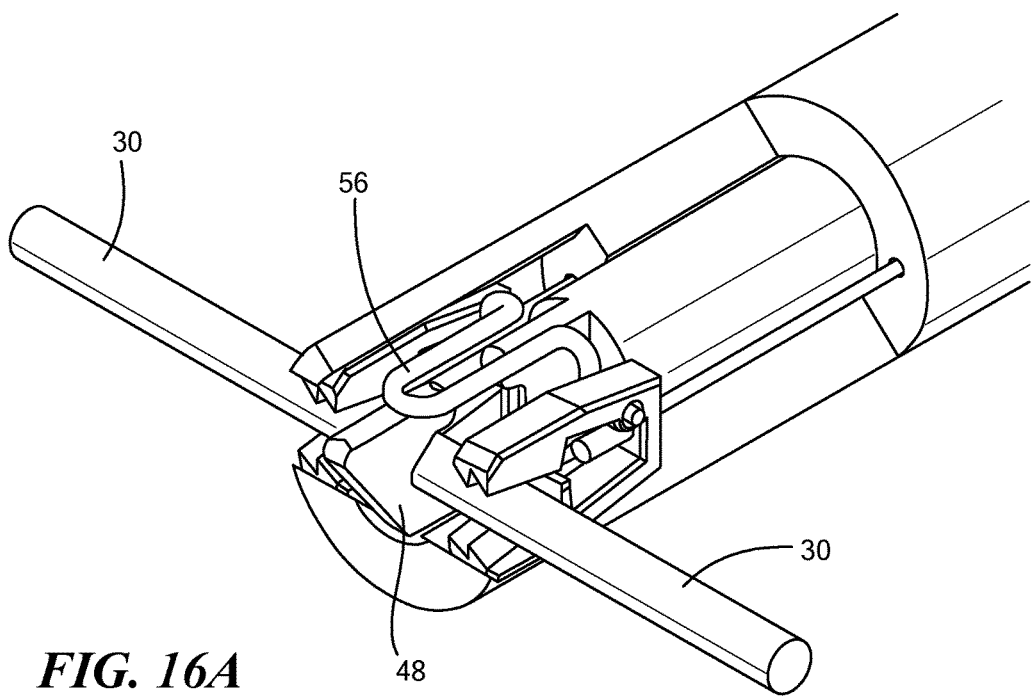
FIG. 16A is a broken-away illustration showing the interior of the device when in the position of FIG. 16.
Figure 17:
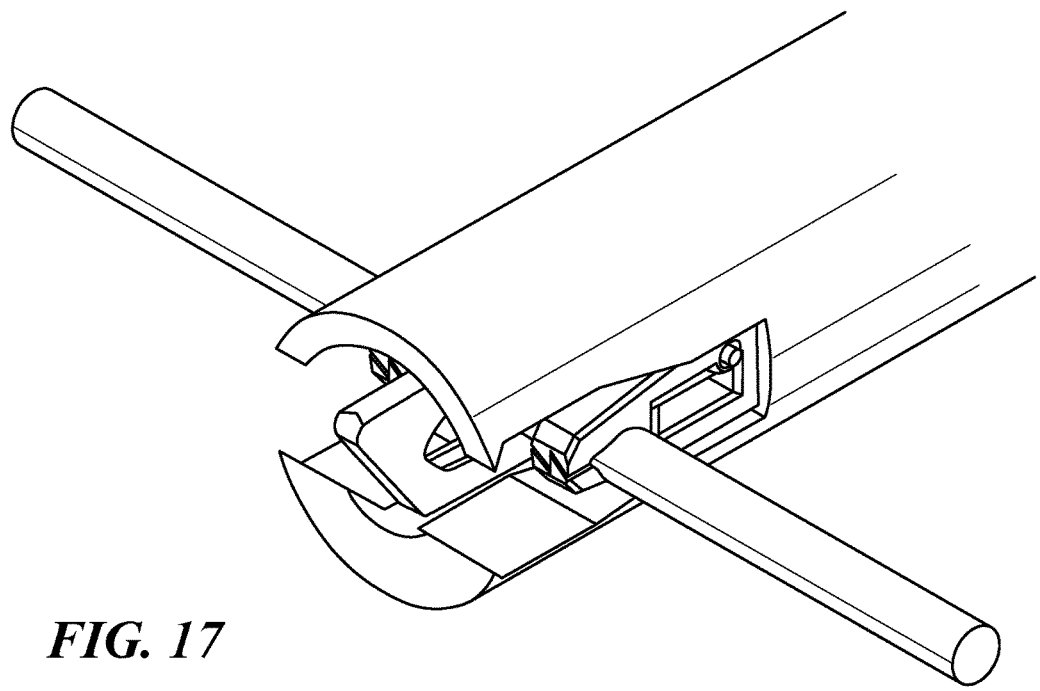
Figure 18:
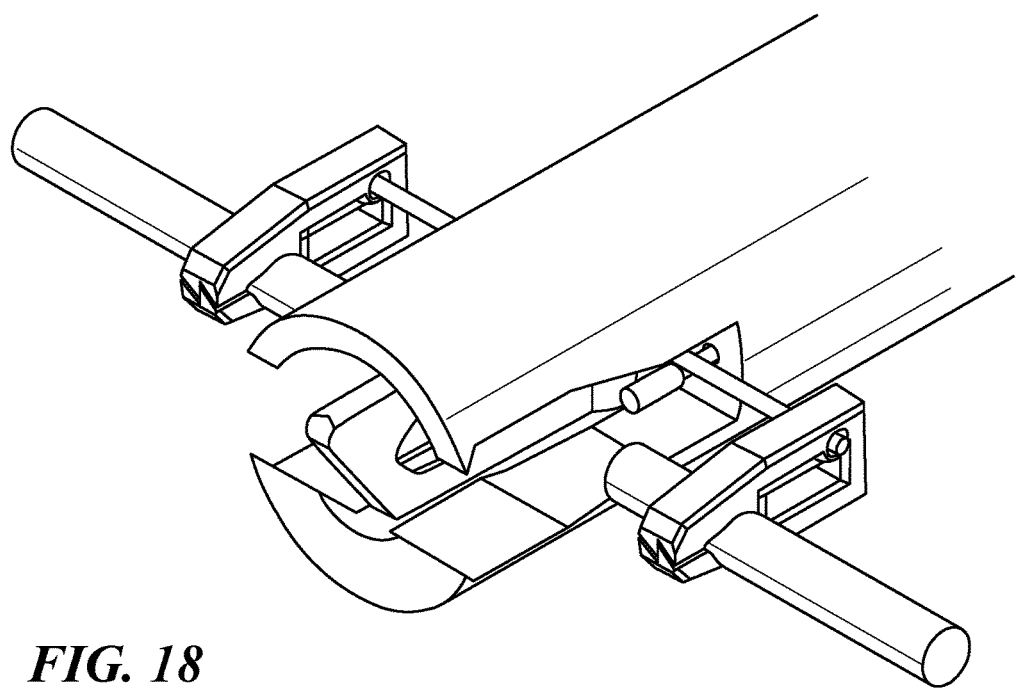

The catheter also carries a prosthetic cord assembly 52 (FIG. 12) that is used to reconnect the severed portions of a natural chord to increase the effective length of that chord. The prosthetic cord assembly 52 includes a pair of clamps 54a, 54b and a prosthetic cord 56 of a selected length secured at its ends to the clamps 54a, 54b. The prosthetic cord may be formed from any suitable biocompatible material such as, for example, expanded polytetrafluoroethylene (EPTFE). Each of the clamps is generally U-shaped to include a pair of legs 58 connected by a closed end (or bight) 60 to define a distally facing opening 62. The clamps 54 are carried at the distal end of the catheter in diametrically spaced, distally facing sockets 64 (FIGS. 5, 9) formed in the wall of the distal end of the outer shaft 40 with the prosthetic cord 56 being folded and disposed within the catheter body as shown in FIGS. 5B and 16A. The sockets 64 and the clamps 54a, 54b are arranged so that they are on opposite sides of the catheter axis and embrace the snare 48 that is movable between the clamps. The clamps are retained by the catheter wall with their openings 62 facing distally so that they may receive a transversely oriented natural chord 30 that has been engaged by and drawn proximally by the snare 48. The clamps preferably may have teeth 72 or other irregular surfaces formed on the inner faces of the clamp legs to enhance the grip on the chord. The teeth may have edges arranged to be oriented transversely to a chord engaged within the clamp.

Figure 9:
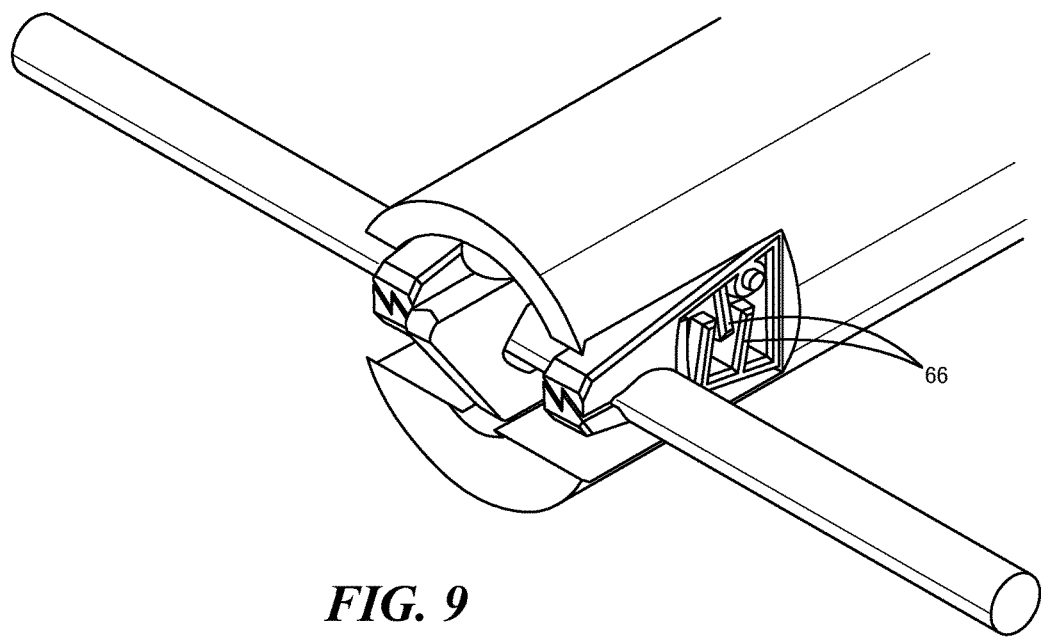
FIG. 9 is an illustration of the distal end of the catheter of one embodiment of the invention showing the chord having been clamped by the clamps.
Figure 10:
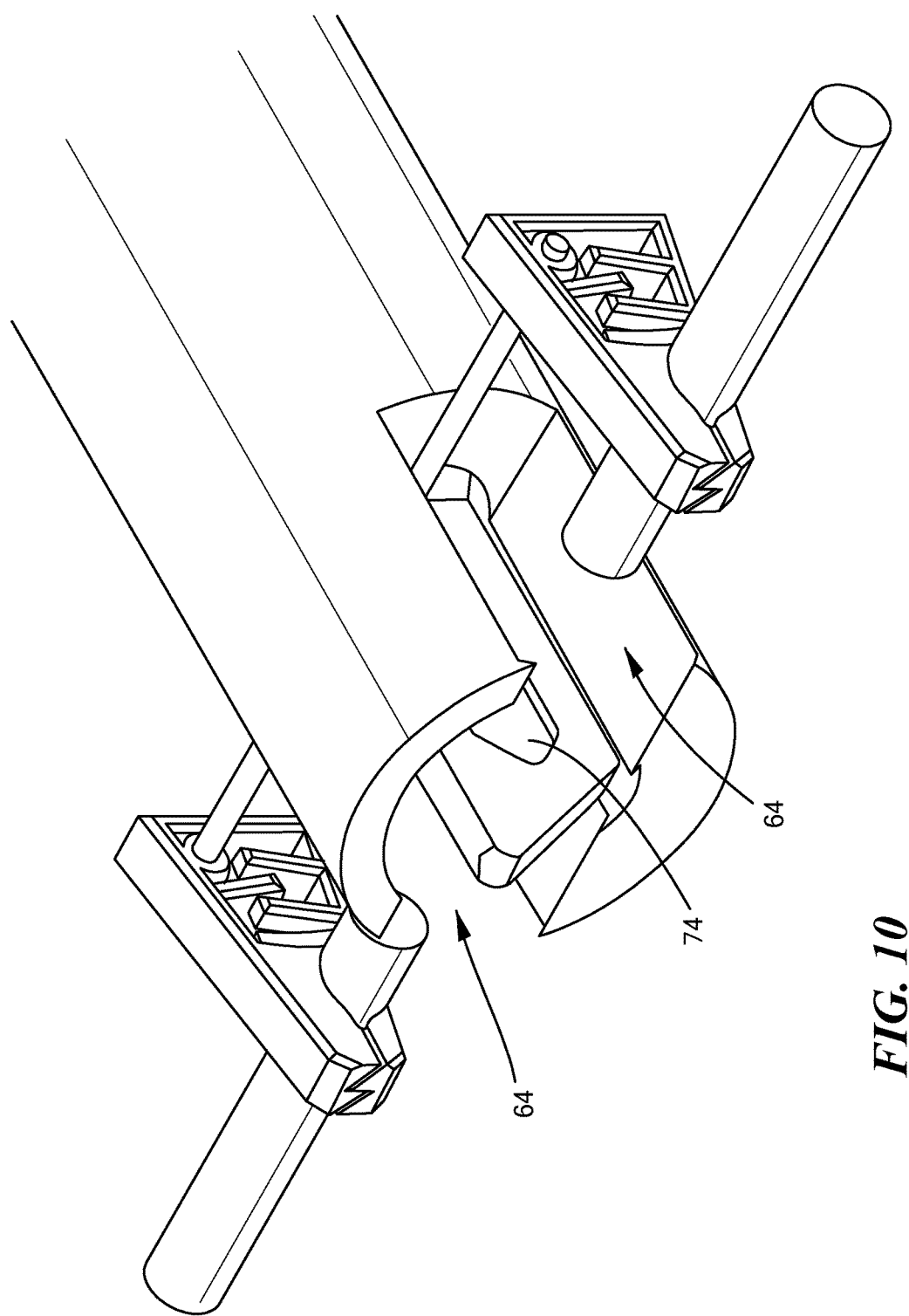
FIG. 10 is an illustration of the distal end of the catheter of one embodiment of the invention showing the chord having been severed and the clamps separated from the catheter.

In one aspect of the invention the clamps 54 may be formed from a biocompatible material having sufficient resilience (e.g., stainless steel) so that the clamp can have a naturally closed, clamped configuration when it is released from the catheter but that can be maintained open while carried by the catheter. To that end, the legs of each clamp may be restrained from closing until a selected snared chord has been drawn into the clamps as indicated in FIGS. 7 and 8. One such restraining mechanism is shown in FIGS. 7 and 8 and includes an arrangement in which the legs 58 of each clamp 54 include inwardly facing ribs 66 that are spaced along the lengths of the legs so that when the clamp is closed the ribs of one leg are interleaved with the ribs of the other leg as shown in FIG. 9. Each of the ribs 66 has a free inner edge 68. When mounted in the catheter the clamp legs 58 are restrained from closing by retractable wires 70 interposed between the opposed inner edges 68 of ribs 66 as shown in FIGS. 7 and 8. In operation, after a selected chord has been drawn into the clamps by the snare 48 (FIGS. 7 and 8) the control handle is operated to retract the wires 70 to release the clamps to close about the chord as shown in FIG. 9. The inherent spring force maintains the clamp in its closed configuration. The transversely spaced teeth 72 enhance the grip of the clamps on the selected chord.

Figure 11:
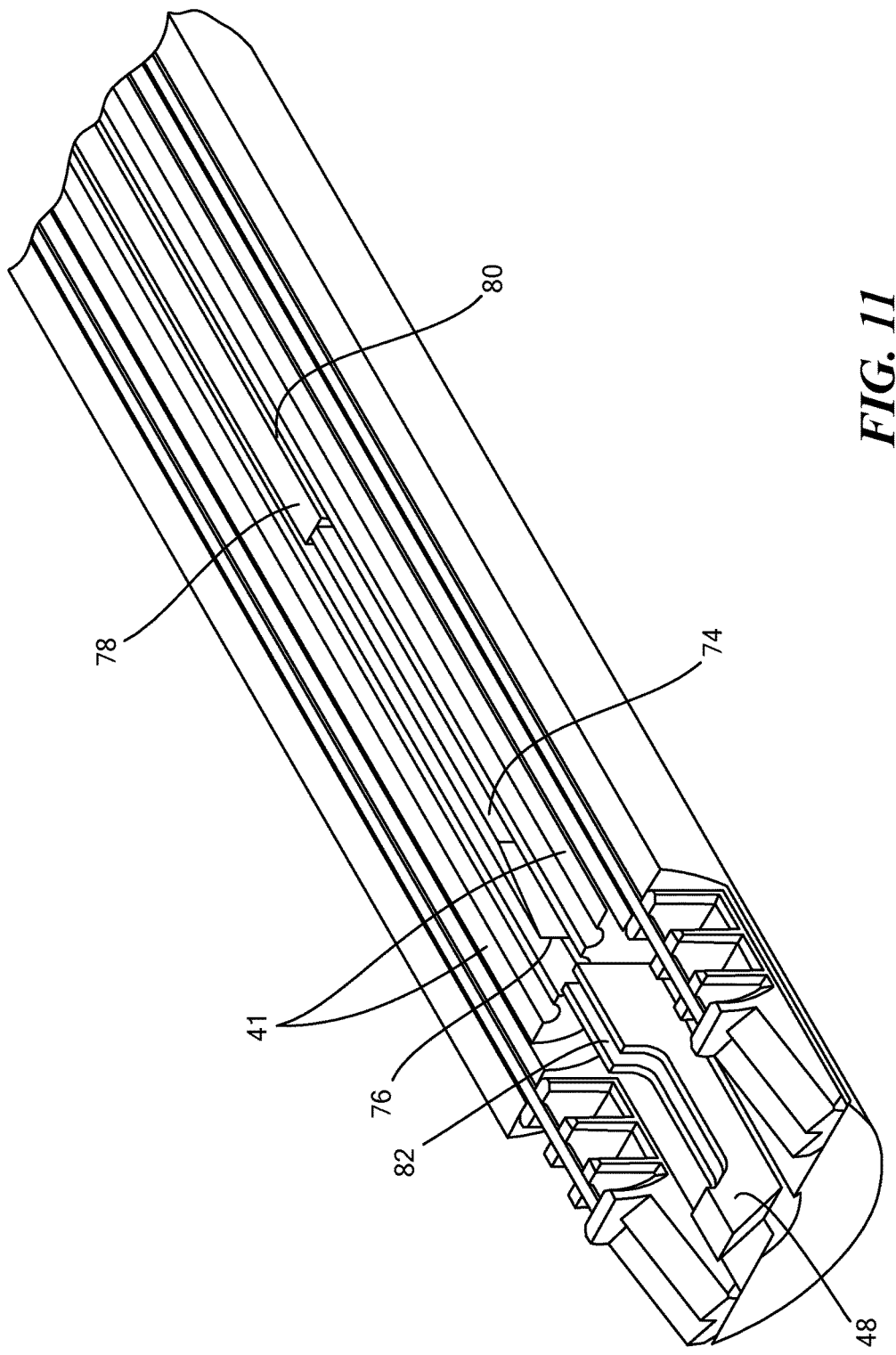
FIG. 11 is a sectional illustration of the distal region of the catheter of FIG. 5 as seen along the line 11-11 of FIG. 5B.
Figure 12:
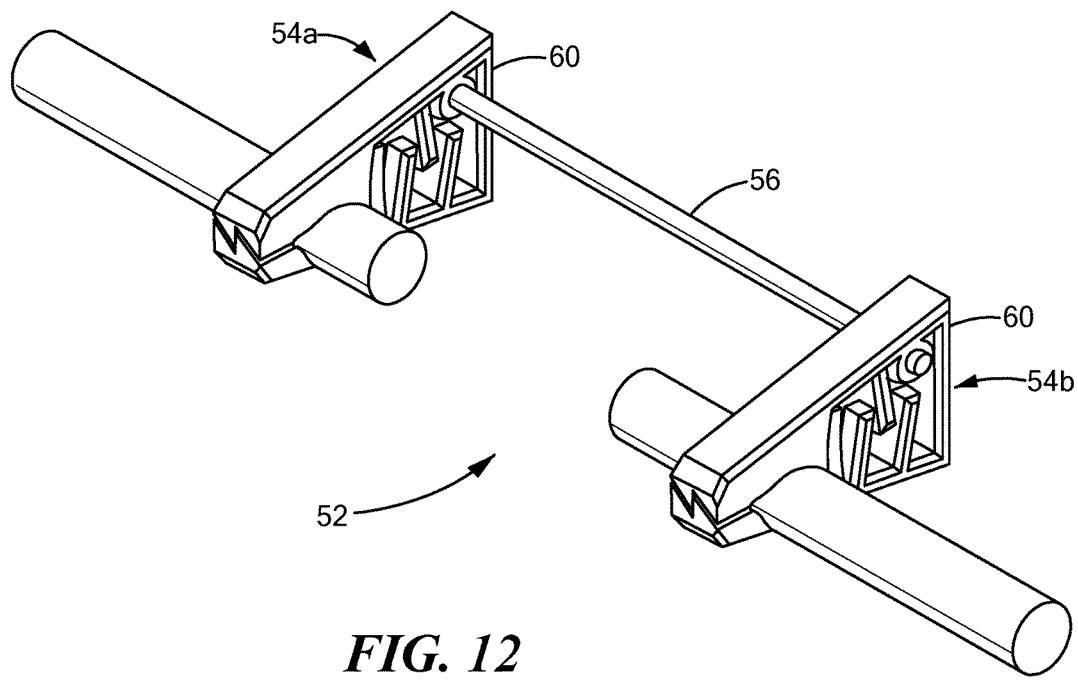
FIG. 12 is a somewhat diagrammatic illustration of the prosthetic cord assembly and severed chord after it has been released by the catheter with the effective length of the chord having been increased.

With the clamps securely attached to a selected natural chord 30, the chord then is severed between the clamps so that when the prosthetic cord assembly 52 and the severed chord are released from the catheter, the effective length of that chord will be increased by an amount dependent on the length of the prosthetic cord assembly 52 and the position of the clamps on the chord. Or slot. As shown in FIG. 11 the natural chord can be severed, for example, by a longitudinally moveable blade 74 having a cutting edge 76 formed on its distal end. The blade 74 is attached to the distal end of a control wire 78 that extends through a lumen 80 in the inner shaft 41. The blade 74 may be arranged to pass through a channel or slot 82 defined within the snare 48 to cut the chord when activated by operation of a control on the control handle. The prosthetic cord assembly then may be released from the catheter (FIG. 12). The length of the prosthetic cord assembly 52 should be selected to modify the effective length of the chord 30 so that the marginal edges of the valve leaflets will coapt during systole. The clinician may perform the procedure with several chordae, as is deemed appropriate by the clinician to restore proper functioning of the valve leaflets.

Figure 14:
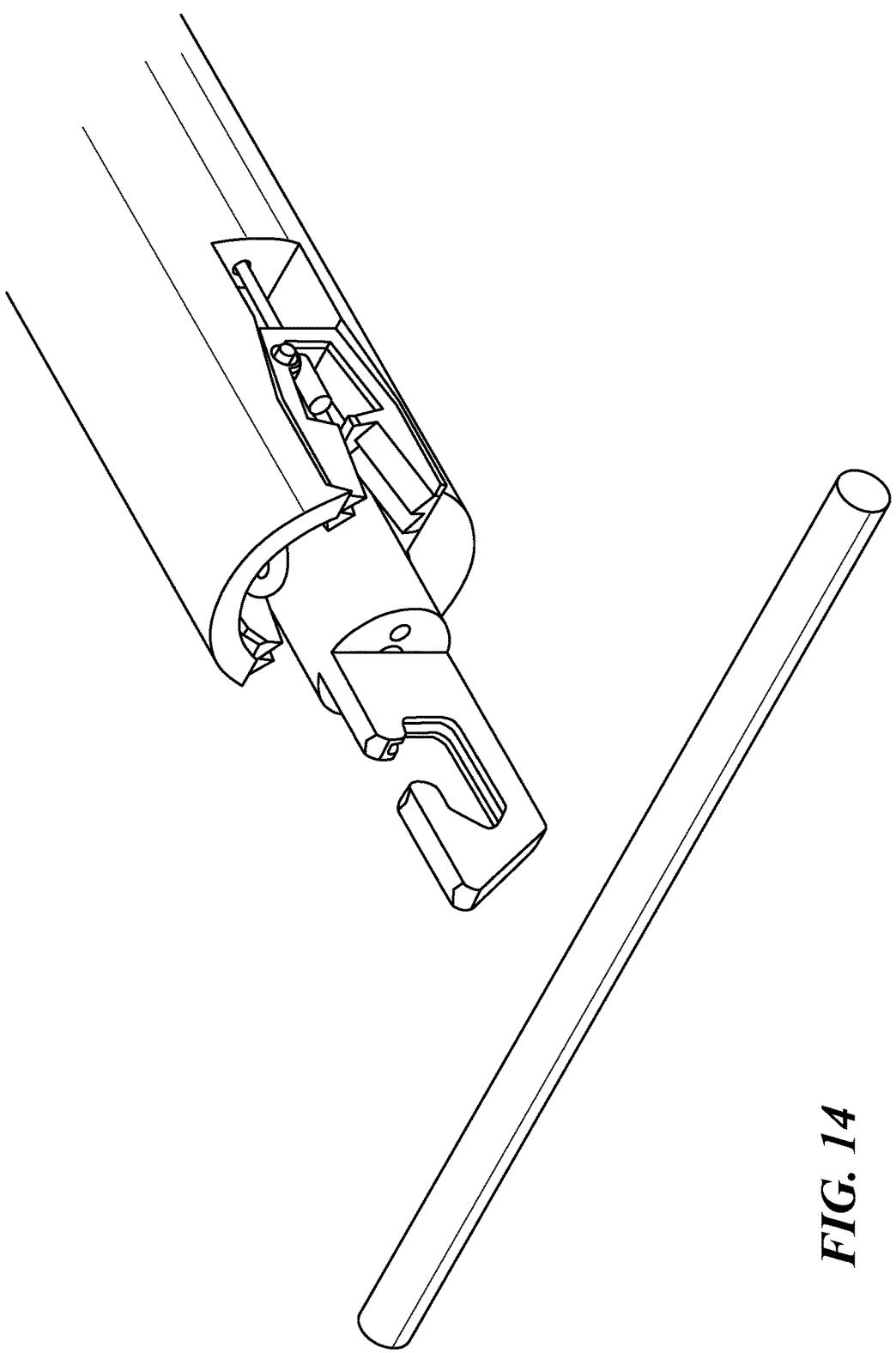
Figure 15:
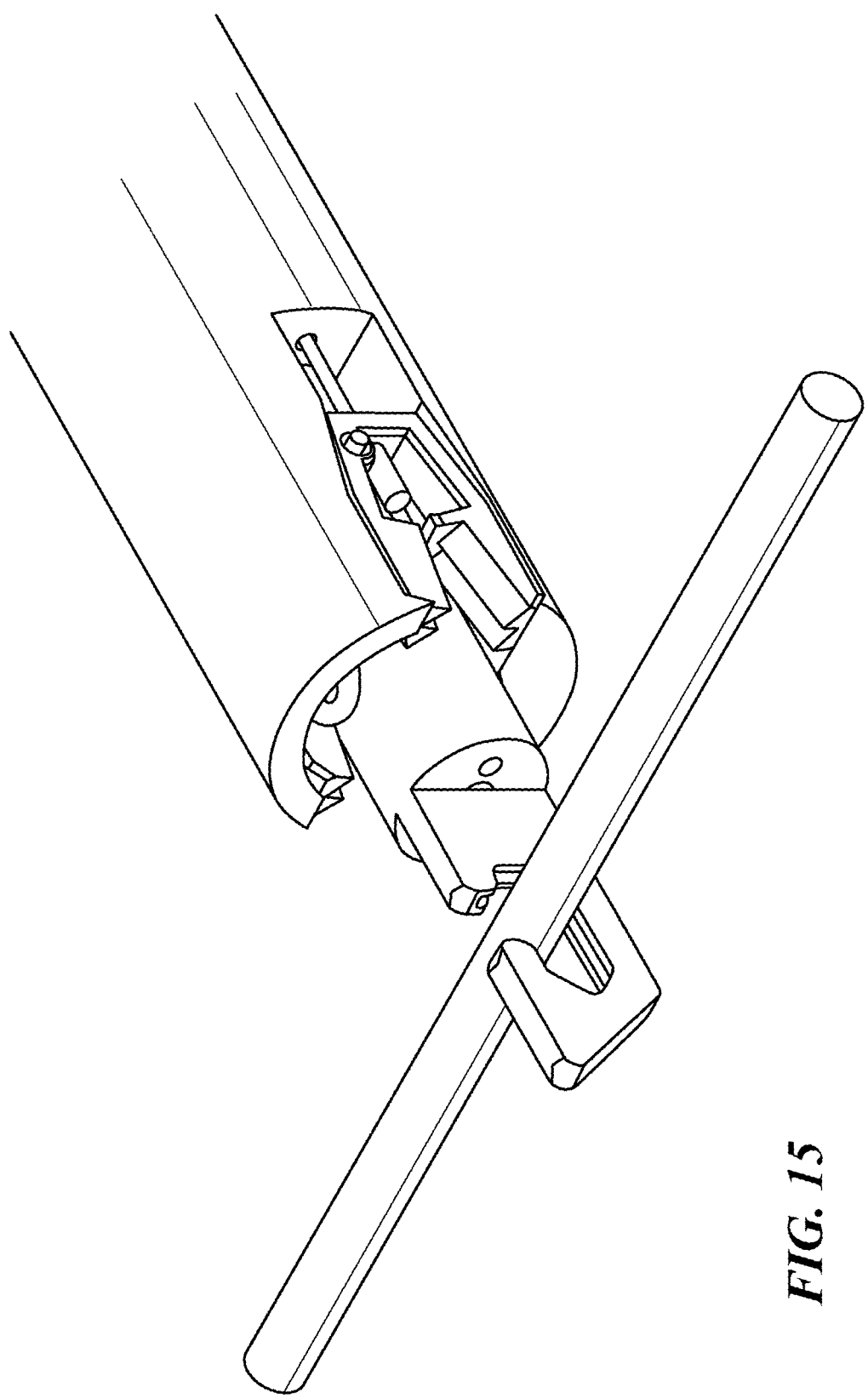

In another embodiment, the clamps may be formed to be permanently deformable from an open to a closed configuration. In this embodiment, shown in FIGS. 13-18 the clamps 84 are formed from a malleable material such as a malleable form of stainless steel so that the legs of the clamps can be crimped securely together. As shown in FIG. 14 the crimpable clamps 84 are held the distal portions 85 of sockets 86 formed at the distal end of the wall of the outer shaft 40. In this embodiment each of the sockets has a proximally extending portion 88 that defines a progressively narrowing region 90. In this embodiment, the bight 92 of each clamp is detachably connected to a pull wire 94 that may be connected to a control on the control handle. The bight 92 of the clamp may have an inwardly extending slot 96 that receives the pull wire 94 and enables the pull wire to slide out of the slot in order to be separated from the clamp 84 when the procedure is completed. The distal end of the pull wires may include enlarged members 95 to enable the clamps to be drawn proximally. As the clamps are pulled proximally each is drawn into the progressively narrowing portion 90 of its socket 86 to wedge the legs of the clamps into a crimped, closed configuration to securely attach to the selected chord.

Figure 21:
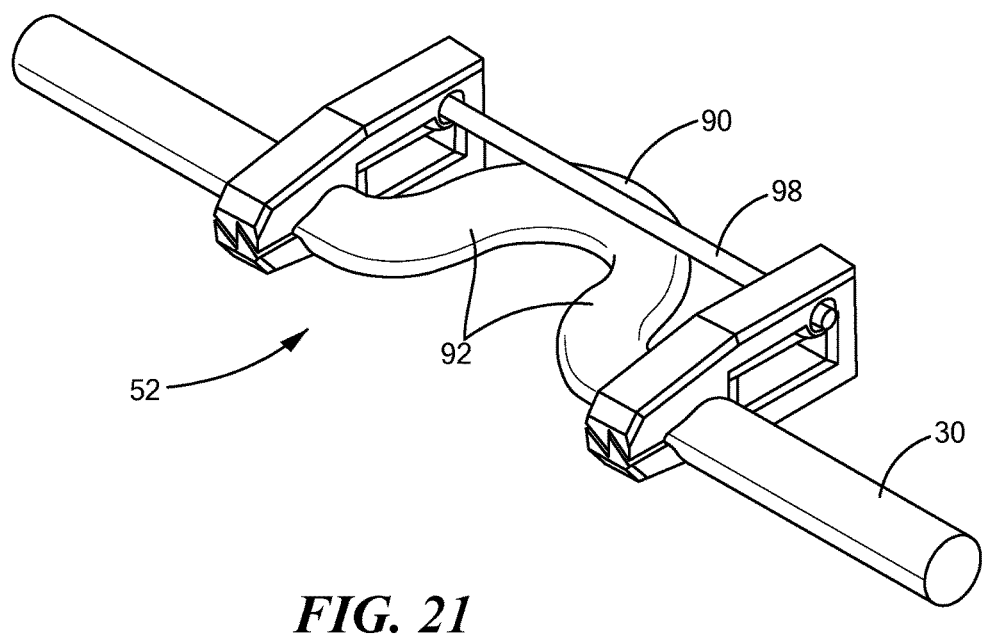
FIG. 21 is a diagrammatic illustration of a chord that has been effectively shortened by the third embodiment of the invention.
Figure 13:
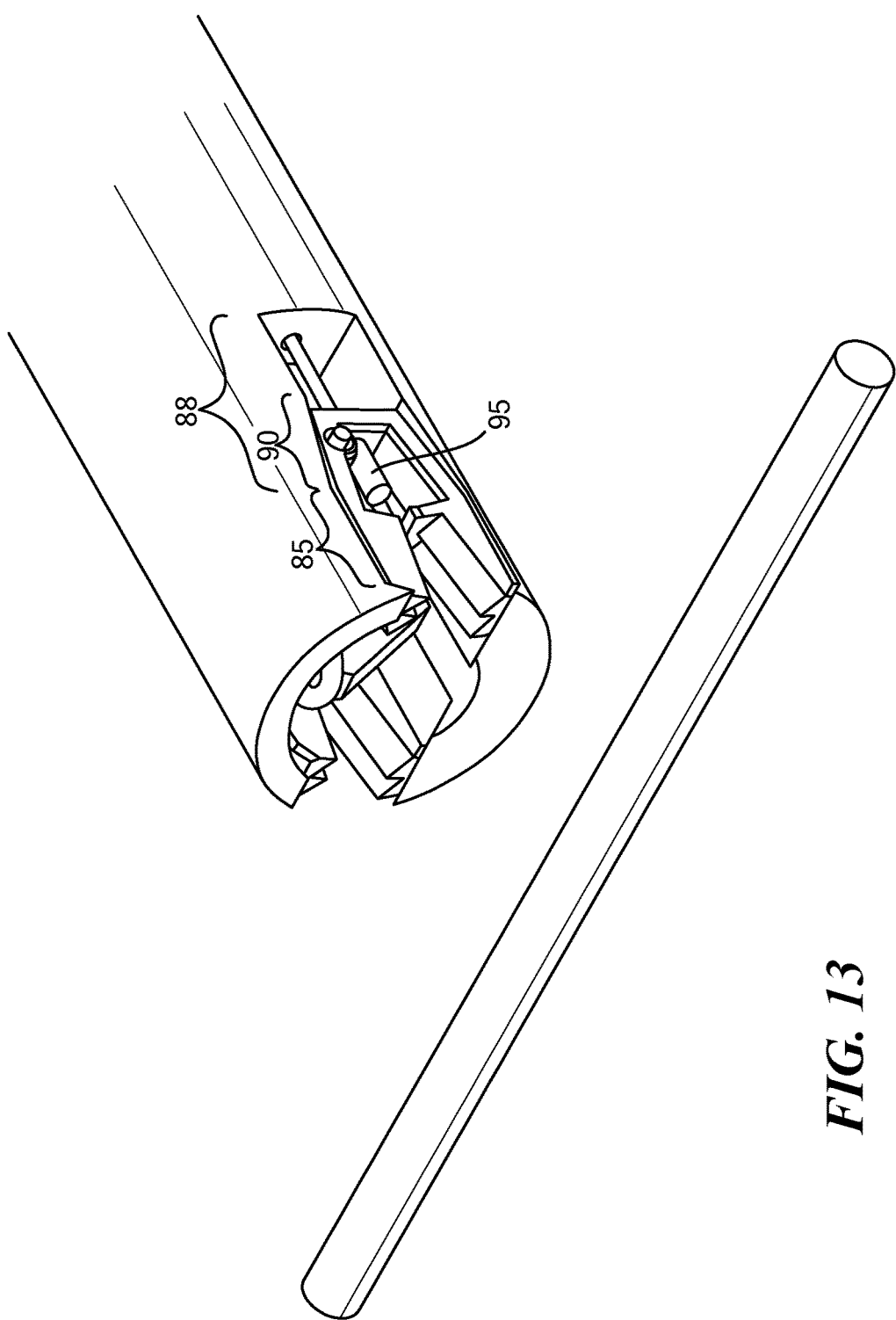
FIG. 13 is an illustration of the distal end of the catheter of a second embodiment of the invention in which the clamps are crimpable.
Figure 19:
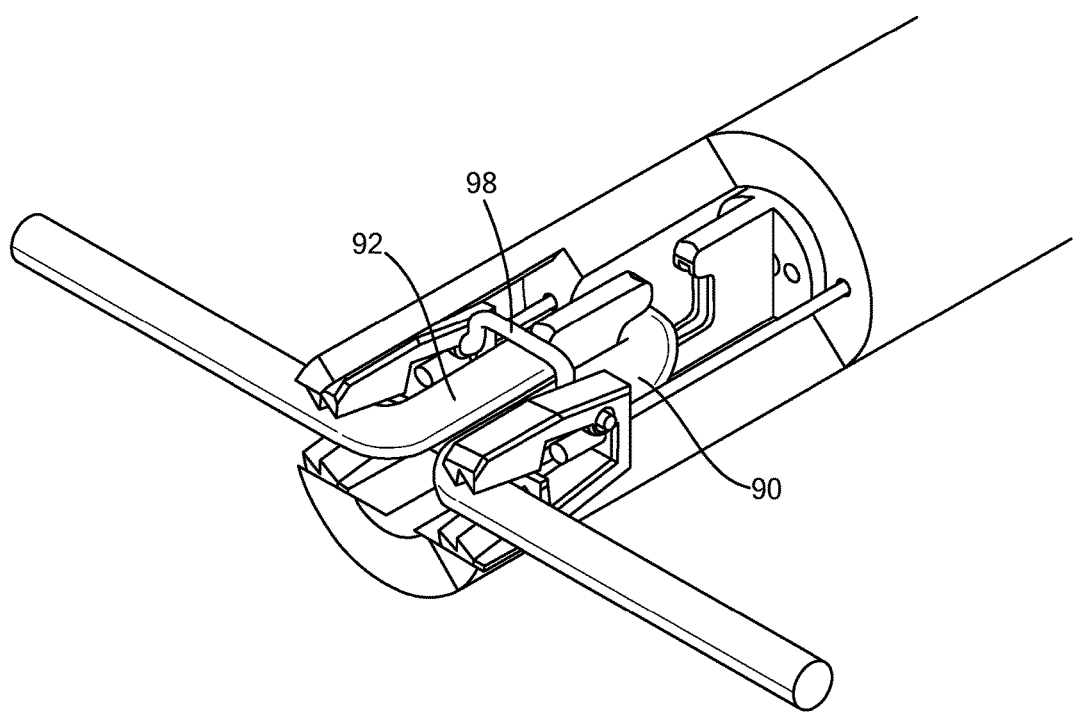
FIG. 19 is a broken-away illustration of a third embodiment of the invention that is adapted to shorten a selected chord associated with an A-V valve.
Figure 20:
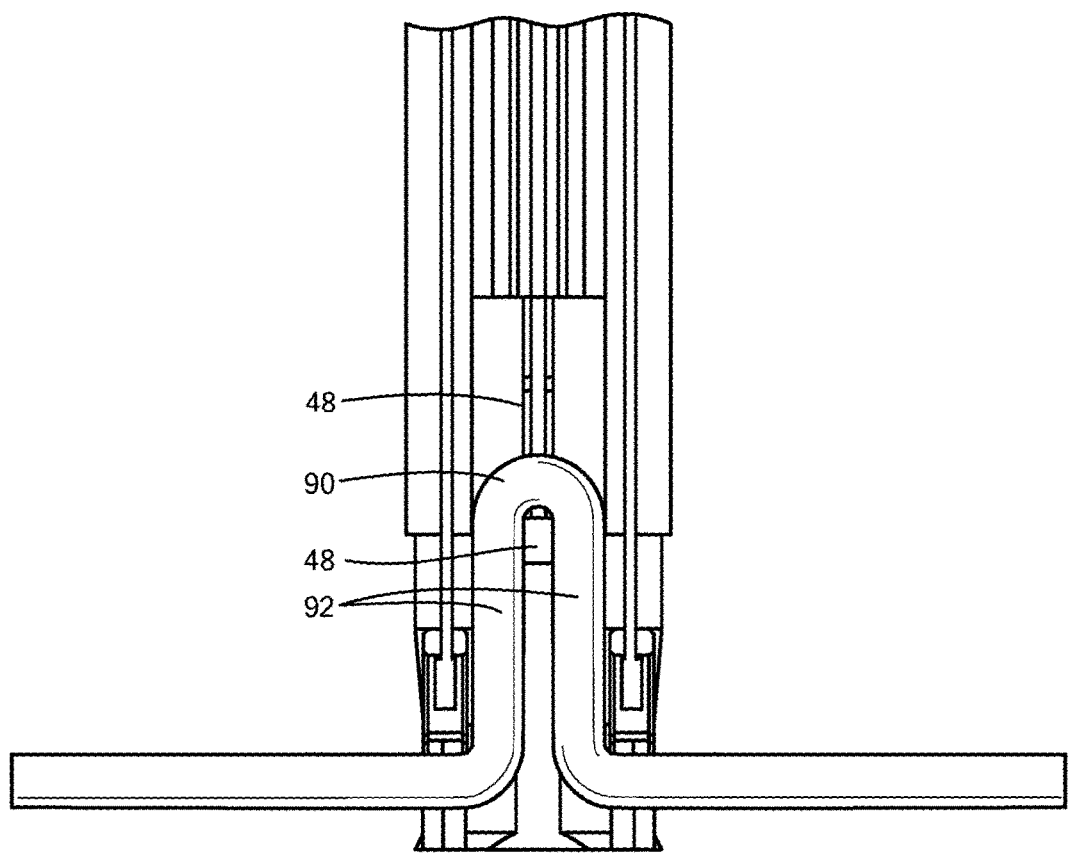
FIG. 20 is a sectional illustration of the catheter of FIG. 19 as seen along an axial, horizontal plane.

In those circumstances where realignment of the leaflets of an A-V valve calls for shortening of one or more selected chordae, a modified form of catheter may be provided. In this arrangement, shown in FIGS. 19-21, the catheter has a snare 48 adapted to engage a selected chord 30 in a manner similar to the previously described embodiments. The snare and catheter shaft are arranged to enable a chord to be captured and to be drawn into the distal end of the catheter to form a hairpin loop with a bight 90 and generally parallel legs 92 (FIG. 19). The extent to which the chord is drawn into the catheter will determine the degree of shortening effected. The range of movement of the snare 48 is greater than that for an embodiment to increase the effective length of a chord. One or more clamps are provided to secure the parallel legs together at a position distally of the bight 92 to shorten the effective length of the selected chord. As shown in FIG. 19 one embodiment of a catheter for shortening the effective length of a chord includes a pair of clamps mounted to the distal end of the outer shaft in a manner similar to that of the previously described embodiments. The clamps may be attached to each other by a short link 98 that maintains the clamps in close proximity to each other. After a selected chord 30 has been drawn into the catheter to form a loop of desired size, the clamps are actuated to secure the legs 92 of the loop together by the clamps. The clamps then are released from the catheter with the effective length of the selected chord having been reduced as suggested in FIG. 21. The clamps may be of either type described above or may utilize alternate constructions.

From the foregoing, it should be appreciated that the invention provides a minimally invasive approach to correcting mitral and tricuspid valve insufficiency. It should be understood, however, that the foregoing description is intended merely to be illustrative and that other modifications and equivalents may be apparent without departing from the principles of the invention.

The invention claimed is:

1. A catheter for selectively adjusting the length of a chord of the chordae tendineae associated with an atrio-ventricular valve, comprising:
   an elongate catheter shaft having proximal and distal ends and a longitudinally extending axis;
   a pair of clamps releasably carried at the distal end of the catheter shaft, the clamps being disposed in transversely spaced relation to each other and on opposite sides of the axis, each clamp having distally facing portions adapted to receive the chord disposed transversely of the catheter axis, the clamps being closeable to securely grip the chord received within the clamps at spaced locations along the chord;
   a chordal snare movable in an axial direction between the spaced clamps between an extended position beyond the distal end of the shaft and a retracted position, the snare being configured to selectively engage the chord, the snare being retractable to draw the engaged chord into the receptive clamps; and
   a prosthetic cord segment attached to each of the clamps, the clamps being operable to close and clamp the chord at spaced locations.

2. The catheter as defined in claim 1 adapted to increase the effective length of the chord further comprising:
   a severing element moveable longitudinally between the clamps and engageable with the clamped chord to sever the selected chord while that chord is clamped;
   the length of the prosthetic cord being such that when released from the catheter the effective length of the chord will have been increased.

3. The catheter as defined in claim 2 further comprising:
   the severing element is moveable longitudinally within a guiding channel formed through the chordal snare.

4. The catheter as defined in claim 1 wherein the severing element is arranged to sever the chord between the clamps.

5. The catheter as defined in claim 1 adapted to decrease the effective length of the chord further comprising:
   the snare being movable into the distal end of the catheter, to draw an engaged chord into a hairpin shape having a pair of legs and a bight, with portions of the chord adjacent the distal ends of the legs being drawn into the receptive clamps;
   the length of the prosthetic cord being less than the length of the hairpin portion of the chord so that when released from the catheter the effective length of the chord will have been decreased.

6. The catheter as defined in claim 1 further comprising:
   the clamps being formed to be inherently resilient and biased toward a closed position;

a removable restraining member associated with each of the clamps to maintain each clamp in an open configuration receptive to the chord;

whereby when the chord is disposed in the receptive clamps, the restraining member can be removed and the clamps will close to grip the chord at spaced locations.

7. The catheter as defined in claim 1 further comprising:

the clamps being formed to be malleable and maintained on the catheter to be open and receptive to the chord;

the clamps being disposed in sockets formed on diametrically opposite sides of the catheter, the clamps being slidable proximally in the sockets, the sockets being tapered in a proximal direction;

whereby when the chord is disposed in the receptive clamps, the clamps can be drawn proximally in their respective slots to enable the tapering portions of the sockets to deform the clamps to grip the chord at spaced locations.

8. A method for selectively increasing the effective length of a chord of the chordae tendineae associated with an atrio-ventricular valve, comprising:

providing a catheter as defined in claim 1 constraining a segment of a selected chord within the clamps;

and severing the chord at a location between the clamps, whereby the effective length of the chord is determined by the length of the prosthetic cord assembly.

9. A method for selectively shortening the effective length of a chord of the chordae tendineae associated with an atrio-ventricular valve, comprising:

constraining a segment of a selected chord into a hairpin-shaped loop having a pair of distally extending legs and a bight;

providing a prosthetic cord assembly including a pair of clamps connected to each other by a prosthetic cord;

applying the clamps to the chord at locations adjacent the distal ends of the legs of the loop; and the prosthetic cord being shorter than the length of the constrained segment of the chord, whereby the effective length of the chord is shortened.

* * * * *